United States Patent [19]

Wedlick

[11] Patent Number: 5,293,840
[45] Date of Patent: Mar. 15, 1994

[54] LABORATORY ANIMAL RESTRAINING JACKET WITH A SEALABLE MEDICAL DEVICE HOLDING POCKET

[76] Inventor: Susan Wedlick, 304 Dayton-Jamesburg Rd., Dayton, N.J. 08810

[21] Appl. No.: 7,681

[22] Filed: Jan. 22, 1993

[51] Int. Cl.5 ............................................. A01K 29/00
[52] U.S. Cl. ..................................... 119/850; 128/874
[58] Field of Search ...................... 119/96, 143; 2/102; 54/79.1, 79.2; 128/847, 874, 877

[56] References Cited

U.S. PATENT DOCUMENTS

| | | | |
|---|---|---|---|
| D. 232,058 | 7/1974 | Palomares | D2/229 |
| 2,170,703 | 8/1939 | Waxman et al. | |
| 2,428,477 | 10/1947 | Thompson | 2/102 |
| 2,448,076 | 8/1948 | Bradley | 2/52 |
| 4,087,864 | 5/1978 | LaBove et al. | 2/102 |
| 4,114,352 | 9/1978 | Horton et al. | 119/143 X |
| 4,473,907 | 10/1984 | Maillard | 248/102 X |
| 4,639,946 | 2/1987 | Koenig | 2/49 R |
| 4,688,270 | 8/1987 | Denicota et al. | 2/102 |
| 4,891,846 | 1/1990 | Sager et al. | 2/49 R |
| 5,007,427 | 4/1991 | Suzuki et al. | 128/659 |
| 5,072,458 | 12/1991 | Suzuki | 2/102 |
| 5,142,702 | 9/1992 | Piloian | 2/102 |

Primary Examiner—Robert P. Swiatek
Attorney, Agent, or Firm—Sperry, Zoda & Kane

[57] ABSTRACT

An animal restraining jacket having openings in the abdominal, neck and arm areas along with a longitudinally extending slit to facilitate placement of the jacket upon a laboratory animal and securement thereon by attaching of a main fastening device which extends along the slit such as a zipper. A flap is positioned on the exterior of the jacket to define a pocket between the jacket and the flap and an access slot is defined in the jacket within the pocket to facilitate communication of a medical device such as a blood catheter from the pocket through the jacket to the interior area for direct access to the laboratory animal. The pocket includes a fastening device such as a zipper which is adapted to close the pocket to prevent infection or tissue damage resulting from an animal scratching or otherwise mishandling of the medical device such as the blood catheter. A cover flap is adapted to extend over the longitudinally extending fastening zipper to prevent tampering thereof by the laboratory animal. Members are included for adjusting the size of the neck aperture and the abdominal aperture and securement members are included for affixing the pocket and main fastening devices in the locked position in such a manner as to allow activities to be performed with respect to the laboratory animals without requiring removal of the animal restraining jacket worn.

20 Claims, 3 Drawing Sheets

LABORATORY ANIMAL RESTRAINING JACKET WITH A SEALABLE MEDICAL DEVICE HOLDING POCKET

BACKGROUND OF THE INVENTION

1. Field Of The Invention

The present invention deals with the field of animal restraining devices used for long term and short term research studies. These restraining devices normally should meet high qualities of standard for comfort and stress which are required by the National Institute of Health in their "Guide For The Care And Use Of Laboratory Animals" regardless of the source of funds which support the research.

These devices must also normally meet the practical needs of an investigator in terms of cost efficiency, reasonable control of the animal and the reliability of research data. The animals must be protected from infection and tissue damage as well as the often associated pain. These animals must also be protected from self-inflicted injuries which can result when they attempt to rid themselves of these devices in the normal desire for self preservation. These devices themselves also must be protected from damage inflicted by the animals or the handlers.

It is, however, desired that a means for chronic online maintenance of fully instrumented research animals be provided which is completely mobile. It is also necessary to provide restraints which reduce the amount of handling required and thereby reduce stress and thusly have the added advantage in that they provide more reliable research data.

2. Description of the Prior Art

Prior art devices for restraint equipment or vests or brackets which are designed to hold equipment have been prevalent in many fields. Examples of such designs are shown in U.S. Pat. No. 2,170,703 patented Aug. 22, 1939 to C. F. Waxman et al on a Garment; U.S. Pat. No. 2,428,477 patented Oct. 7, 1947 to J. H. Thompson on a Concealed Pocket For Garments; U.S. Pat. No. 2,448,076 patented Aug. 31, 1948 to R. I. Bradley on a Bib And Safety Jacket; U.S. Pat. No. 232,058 patented Jul. 16, 1974 to C. Palomares on a Bottle-Holding Infant Jacket; U.S. Pat. No. 4,087,864 patented May 9, 1978 to L. LaBove et al on a Dispensing Vest For Patients Receiving Hyperalimentation; U.S. Pat. No. 4,473,907 patented Oct. 2, 1984 to S. Maillard on a Combined Insulated Enclosure And Bib For Support Of A Nursing Bottle; U.S. Pat. No. 4,639,946 patented Feb. 3, 1987 to L. Koenig on a Restraining Garment With Detachable Bib; U.S. Pat. No. 4,688,270 patented Aug. 25, 1987 to P. Denicola et al and assigned to Children's Hospital Medical Center on a Garment For Shielding Lines Connected To A Patient During Invasive Therapy; U.S. Pat. No. 4,891,846 patented Jan. 9, 1990 to A. Sager et al on a Medical Absorption Garment; U.S. Pat. No. 5,007,427 patented Apr. 16, 1991 to A. Suzuki et al and assigned to Capintec, Inc. on an Ambulatory Physiological Evaluation System Including Cardiac Monitoring and U.S. Pat. No. 5,072,458 patented Dec. 17, 1991 to A. Suzuki and assigned to Capintec, Inc. on a Vest For Use In An Ambulatory Physiological Evaluation System Including Cardiac Monitoring.

SUMMARY OF THE INVENTION

The present invention provides an improved laboratory animal restraining jacket with a sealable medical device holding pocket including a jacket member preferably of an open weave polyester material which includes a front section and a rear section. The front and rear section when attached with respect to one another define the jacket member and specifically define a neck opening therebetween. The jacket also includes an abdominal opening and preferably two arm openings. The rear section of the jacket also includes a main opening slit extending from the neck opening all the way to the abdominal opening to provide a means to facilitate putting on and off of the jacket with respect to the laboratory animal.

The jacket further defines a peripheral abdominal channel which defines two apertures therein in which is positioned an abdominal band. This abdominal band is positioned extending through the abdominal channel apertures and through the peripheral abdominal channel in such a manner as to act as a drawstring to tighten the abdominal aperture for providing a more close fit of the abdominal aperture about the abdomen of the laboratory animal. The abdominal band preferably includes a plurality of button holes on one end and a button on the opposite end to facilitate securement with respect to itself to achieve the adjustability of the size of the abdominal opening.

The jacket also includes a peripheral neck channel extending around the neck opening including two apertures with a neck band positioned extending therethrough. The neck band is constructed similar to the abdominal band and is designed to vary the size of the neck opening to tighten the neck opening about the neck of the laboratory animal. The neck band preferably includes a plurality of neck button holes on one end thereof and a neck button on the other end thereof to facilitate tightening of this neck band and the neck opening about the neck of the laboratory animal as desired.

A main fastening device such as a zipper is positioned adjacent the main opening slit of the rear section of the jacket. The main zipper is adapted to selectively close or open the main opening slit as desired in order to facilitate placement and removal of the jacket upon a laboratory animal. The main zipper is preferably in a closed position responsive to being in the lowermost position adjacent the abdominal opening. The main zipper includes a main tab which is preferably movably secured with respect thereto to facilitate locking of the zipper in the closed position.

A flap member is included positioned on the exterior of the jacket such as to define a pocket between the flap and the jacket. The flap and the jacket also define a pocket opening to facilitate access to the interior of the pocket. The jacket defines an access slot extending through the jacket adjacent the flap and within the pocket to allow placement of a medical device such as a blood catheter and communication line within the pocket to extend through the access slot for direct access to the body of a laboratory animal positioned within the jacket member without requiring removal of the jacket. This access slot preferably will extend vertically within the pocket.

A pocket fastening device such as a pocket zipper will extend along the pocket opening for closing of the pocket opening and eliminating possible mishandling or destruction of the medical equipment positioned therein by the laboratory animal when wearing the jacket. The pocket zipper is preferably in a closed position responsive to being in the uppermost position which is closest to the neck opening of the jacket. The pocket zipper also includes a pocket tab preferably being movably attached thereto.

A main covering member is positioned adjacent the main opening slit and adjacent the main zipper. This main cover is preferably integral with respect to the jacket and is adapted to extend over the main zipper and engage the jacket member thereacross to prevent access of the laboratory animal to the main zipper on the exterior of the jacket. To facilitate this engagement a main hook and loop engagement device may be positioned adjacent the main covering device and the jacket to facilitate engagement therebetween to aid in selective covering of the main zipper as desired.

A main clip may be attachable with respect to the abdominal band and with respect to the main tab in order to retain the main zipper in the closed position adjacent the abdominal opening while the jacket is being worn by the laboratory animal and the animal relatively unattended. Furthermore a pocket retaining loop may be attached with respect to the jacket member adjacent the pocket means. This pocket retaining loop is preferably engageable with respect to the pocket tab to retain the pocket zipper in the closed position when desired. Furthermore a locking tie device may be engageable with respect to the pocket tab and with respect to the jacket member to facilitate selective holding of the pocket zipper in the closed position.

Alternatively, the present design may include a strengthening layer of denim or other material which extends over the majority of the portion of the front section of the jacket to aid in strengthening and durability thereof.

It is an object of the present invention to provide an improved laboratory animal restraining jacket with a sealable medical device holding pocket wherein maintenance costs are minimized.

It is an object of the present invention to provide an improved laboratory animal restraining jacket with a sealable medical device holding pocket wherein initial cost for equipment is minimized.

It is an object of the present invention to provide an improved laboratory animal restraining jacket with a sealable medical device holding pocket wherein comfort to the laboratory animal is maximized.

It is an object of the present invention to provide an improved laboratory animal restraining jacket with a sealable medical device holding pocket wherein back-up securement device are included for retaining the attachment zippers in the closed position.

It is an object of the present invention to provide an improved laboratory animal restraining jacket with a sealable medical device holding pocket wherein access to the main torso of the laboratory animal is provided through a slot defined in a medical equipment holding pocket.

It is an object of the present invention to provide an improved laboratory animal restraining jacket with a sealable medical device holding pocket wherein variation in sizing of the neck opening is easily achievable.

It is an object of the present invention to provide an improved laboratory animal restraining jacket with a sealable medical device holding pocket wherein variation in the sizing of the abdominal opening is easily achievable.

It is an object of the present invention to provide an improved laboratory animal restraining jacket with a sealable medical device holding pocket wherein durability is significantly enhanced.

It is an object of the present invention to provide an improved laboratory animal restraining jacket with a sealable medical device holding pocket wherein removal of the jacket is not required to provide medical access to the blood system of a laboratory animal.

It is an object of the present invention to provide an improved laboratory animal restraining jacket with a sealable medical device holding pocket wherein dangers to laboratory personnel is minimized.

It is an object of the present invention to provide an improved laboratory animal restraining jacket with a sealable medical device holding pocket wherein stress is significantly reduced in laboratory animals.

It is an object of the present invention to provide an improved laboratory animal restraining jacket with a sealable medical device holding pocket wherein reasonable control of the animal is maintained while complete medical access to the bloodstream is also maintained.

It is an object of the present invention to provide an improved laboratory animal restraining jacket with a sealable medical device holding pocket wherein the reliability of research data resulting from testing on the so-restrained laboratory animal is significantly enhanced.

It is an object of the present invention to provide an improved laboratory animal restraining jacket with a sealable medical device holding pocket wherein the practical needs of investigators are adequately maintained.

It is an object of the present invention to provide an improved laboratory animal restraining jacket with a sealable medical device holding pocket wherein laboratory animals receive significant protection from infection.

It is an object of the present invention to provide an improved laboratory animal restraining jacket with a sealable medical device holding pocket wherein laboratory animals receive significant protection from tissue damage.

It is an object of the present invention to provide an improved laboratory animal restraining jacket with a sealable medical device holding pocket wherein laboratory animals receive significant protection from investigative pain.

It is an object of the present invention to provide an improved laboratory animal restraining jacket with a sealable medical device holding pocket wherein laboratory animals receive protection from self-inflicted injuries.

It is an object of the present invention to provide an improved laboratory animal restraining jacket with a sealable medical device holding pocket wherein laboratory animals are maintained completely mobile.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
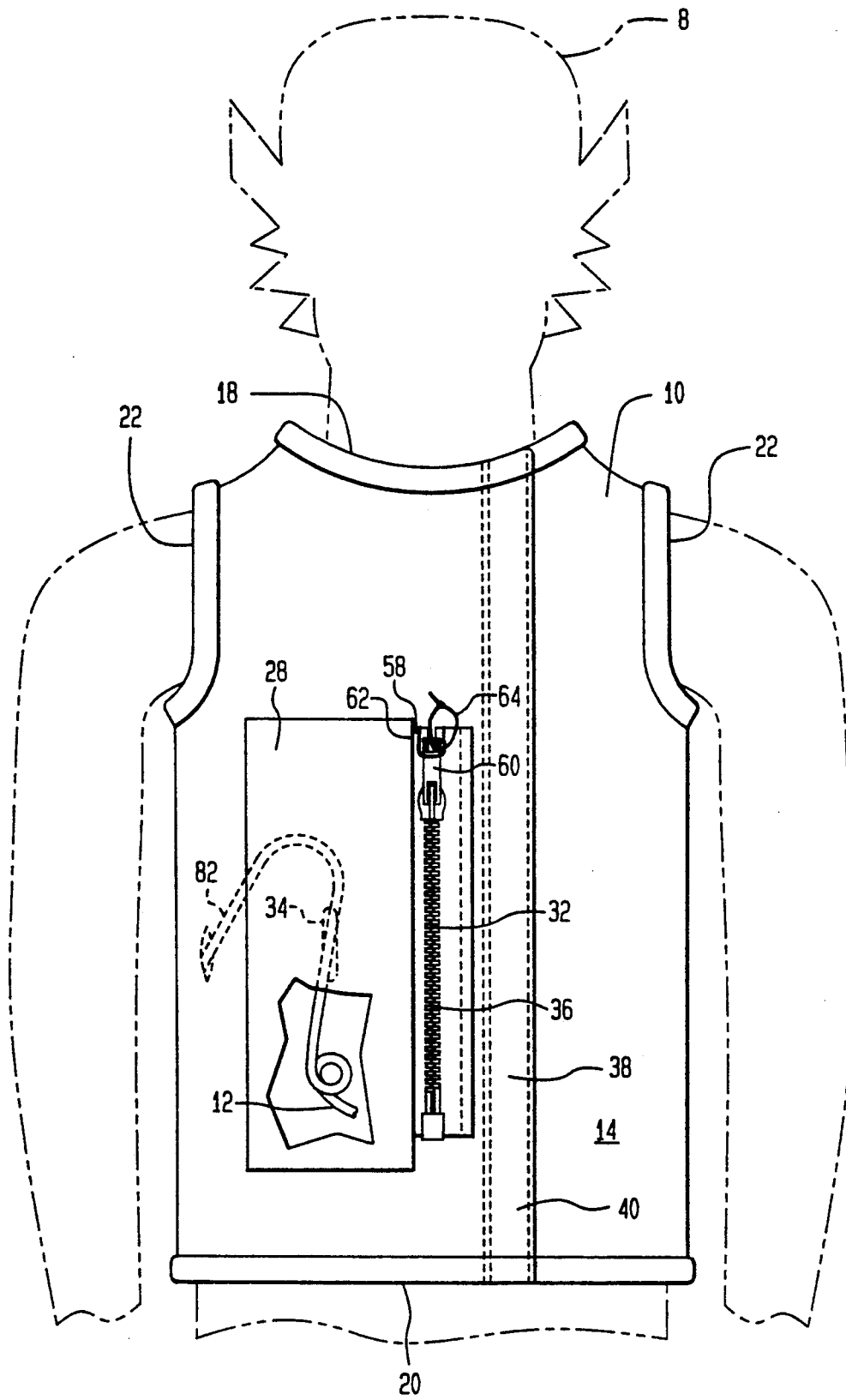
FIG. 1 is a rear plan view of an embodiment of the improved laboratory animal restraining jacket of the present invention.
Figure 2:
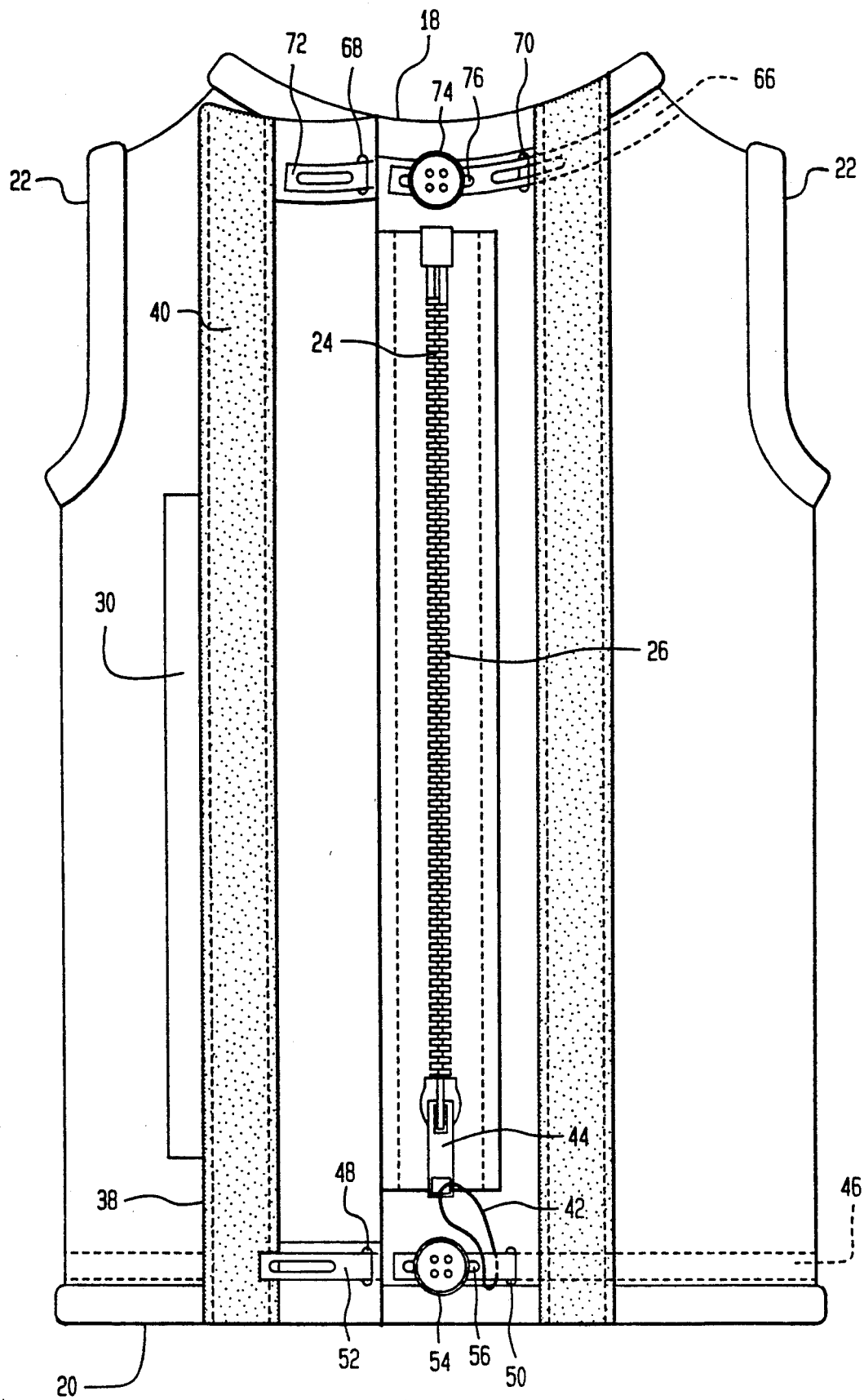
FIG. 2 is a detailed rear plan view of the embodiment shown in FIG. 1.
Figure 3:
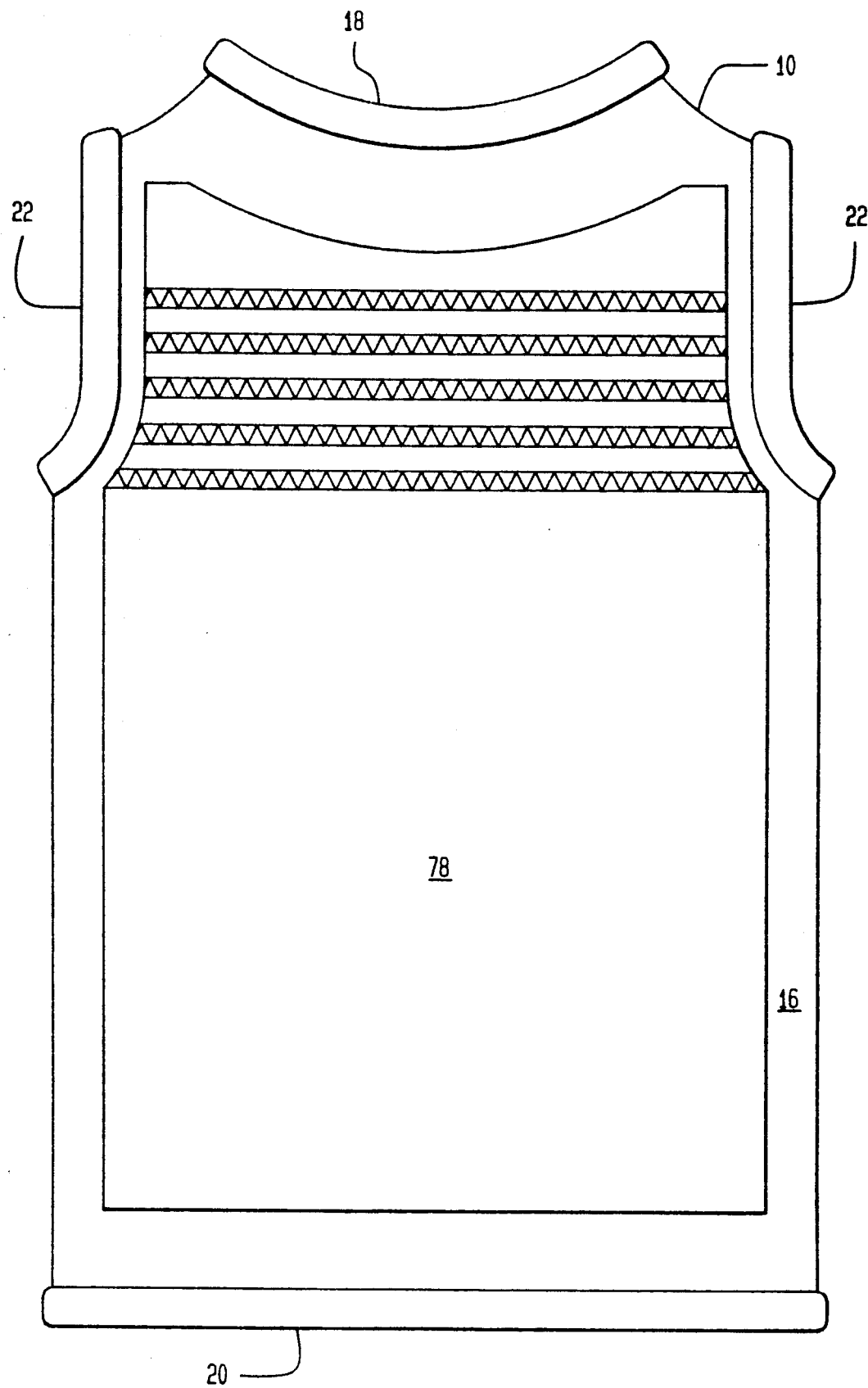
FIG. 3 is a front plan view of the embodiment shown in FIG. 1.

The present invention provides a jacket 10 adapted to be worn by a laboratory animal 8 to facilitate the placement of medical device 12 safely and securely therein. It is conventional with laboratory animals to provide restraining jackets 10 while at the same time placing medical devices 12 which may include a catheter 82 adjacent to the laboratory animal.

Access to the blood system of the laboratory animal is the primary motivating force behind handling of the laboratory animals by investigators and animal handlers. The present invention provides a restraint jacket 10 which includes a unique configuration which allows the placement of the medical device 12 in a safe location on the jacket within a pocket 30 with the medical line running to a catheter 82 which is fixedly positioned in the body of the laboratory animal 8 such as to be retained therein. The unique design of the jacket 10 of the present invention minimizes the dangers that a laboratory animal has heretofore been exposed to by self inflicted injuries resulting from attempting to remove the jacket 10 or resulting in attempts to remove the medical device 12. Both the jacket 10 and the medical device 12 are retained by the unique configuration of the present invention in such a manner as to prevent damage resulting from laboratory animals attempting to rid themselves of the medical device 12 or even the jacket 10, itself.

The jacket 10 of the present invention includes a rear section 14 and front section 16. These two sections are joined with respect to one another in such a manner as to define a neck opening 18 through which the neck of the laboratory animal 8 is adapted to extend. In a similar fashion rear section 14 and the front section 16 define an abdominal opening 20 as well as preferably two arm openings 22. A main opening slit 24 extends from the neck opening 18 to the abdominal opening 20 to facilitate placement of the jacket 10 upon the laboratory animal 8 and also to aid in removal of the jacket 10 from the animal. This main opening slit can be closed by a main fastening means such as a zipper 26 which extends longitudinally adjacent the main opening slit 24. When the jacket member 10 is positioned on the laboratory animal 8 and the main fastening zipper 26 is zipped it is preferable that access by the laboratory animal to that zipper is minimized. For this purpose a main covering means 38 is adapted to extend over the main fastening zipper 26 to eliminate the possibility of the animal scratching or clawing at the zipper 26 and possibly actually removing of the jacket 10 or damaging of the jacket or zipper. To facilitate positioning of the main covering means 38 a main hook and loop engagement means 40 may be attached with respect to the jacket 10 and the main covering means 38 in such a manner as to secure them with respect to one another and thereby further minimize the possibility of the laboratory animal 8 gaining direct access to the main fastening zipper 26.

Preferably the pocket 30 is formed by the positioning of a flap 28 in securement with respect to a portion of the jacket member 10. Flap 28 and the adjacent area of the jacket 10 form the pocket 30 and also form the pocket opening means 32. This pocket is adapted to retain therein the medical device 12 such as a catheter 82.

Opening and closing of the pocket opening 32 is controlled by a pocket fastening means such as a zipper 36. When closed the pocket fastening zipper 36 will close the pocket opening 32 and prevent the laboratory animal from having any access thereto.

An access slot 34 is defined in the portion of the jacket area 10 immediately adjacent the flap 28 which defines the pocket 30. Access slot 34 provides a means for medical communication between the medical device 12 and the body of the laboratory animal 8. By providing of access slot 34 access to the bloodstream of the laboratory animal 8 can be achieved without requiring removal of the jacket 10.

In the conventional configuration the catheter 82 will be positioned within the pocket 30. The syringe will be positioned in the body of the laboratory animal within the jacket. A medical line will extend from the catheter 82 through the access slot 34 and into the syringe thereby providing direct access to the bloodstream of the laboratory animal 8 without requiring removal of the jacket 10. Furthermore, correct operation of the main fastening zipper 26 and the pocket fastening zipper 36 will minimize any chances of the laboratory animal removing the jacket 10 or gaining access to the medical device 12.

The jacket 10 of the present invention preferably defines a peripheral abdominal channel 46 extending therearound. This channel preferably includes a first abdominal channel aperture 48 and a second abdominal channel aperture 50. An abdominal band member 52 is adapted to extend through the peripheral abdominal channel 46 and through the first abdominal channel 48 and the second abdominal channel 50 in such a manner as to be engageable with respect to itself to restrict the size of the abdominal opening 20. To facilitate in this configuration the abdominal band may preferably define a plurality of abdominal button holes 56 as well as an abdominal button member 54 engageable with respect to one or more of the button holes 56 to control the size of the abdominal opening 20.

In a similar manner a peripheral neck channel means 66 may be defined immediately adjacent the neck opening 18. This peripheral neck channel means 66 will preferably include a first neck channel aperture 68 and a second neck channel aperture 70. A neck band member 72 will be positioned extending through the peripheral neck channel 66 as well as through the first neck channel 68 and the second neck channel 70 in such a manner as to be engageable with respect to itself to facilitate control of size of the neck opening 18. The neck band member 72 will preferably include a plurality of neck button holes 76 as well as a neck button means 74 which are engageable with respect to one another to control securement of the neck band member 72 with respect to itself.

It is important to appreciate that control of the sizing of particularly the neck opening 18 and the abdominal opening 20 is extremely important. It is these two openings through which a normal laboratory animal 8 such as a monkey or the like often attempts to extend fingers, hands or other implements in such a manner as to attempt to discard the jacket 10 or the medical equipment 12. By maintaining these two openings in a tight fitting fashion with respect to the body of the laboratory animal, minimization of damage caused by reaching through these openings is achieved.

To further control damage caused by the laboratory animal either to itself or to the equipment or jacket 10, the present invention includes multiple back-up systems and securement means for holding of the zippers on the pockets and on the jacket in the closed position.

The main source of protection of the main fastening zipper 26 is the main covering means 38 extending thereover to restrict access thereto by the laboratory animal. A secondary back-up restriction means is by the inclusion of a main clip means 42. The main clip means 42 is preferably securable with respect to a main tab means 44 of the main fastening zipper 26. The main clip means 42 is also secured preferably with respect to the jacket 10 and most particularly is usually directly attached with respect to the abdominal band member 52 since it is normally located immediately adjacent the closed or down position of the main fastening zipper 26. This main clip member 42 thereby provides a means for positive locking of the main fastening zipper 26 in the closed or down position.

The pocket fastening zipper 36 also includes a back-up locking system. The back-up locking system is defined as the pocket retaining means 58 which may take the form of a loop member 62. The loop means 62 is adapted to extend over the pocket tab means 60 included in the pocket fastening zipper 36 in such a fashion as to retain the pocket fastening zipper 36 in the uppermost position which is the locking position for the pocket zipper. A back-up system is provided by a locking tie means 64 which is adapted to extend through the pocket tab means 60 and through the material of the jacket 10 immediately thereadjacent and back again through the material of the jacket 10 to be locked upon itself and thereby provide an additional tie means for securing of the pocket tab means 60 in the uppermost position and thereby maintain locking of the pocket fastening zipper 36 in the secured or closed position.

Further access to the pocket and medical equipment as well as to the zippers of the jacket 10 of the present invention is included by positioning these zippers preferably on the front section 16 of the jacket 10. Often, however, it has been found that the front section 16 tends to wear out more quickly than the rear section because of the excessive use and the fact that the animal is often sitting or lying upon the front section 16 for extended periods of time. As a result the present invention further contemplates the placement of an additional layer of material 78 across at least a portion of the front section 16. Preferably this additional layer of material will be of a denim or other durable material to facilitate the life of the jacket garment 10.

In operation with the design of the present invention the jacket 10 normally in the open position will be placed upon a laboratory animal 8 such as a laboratory monkey. While in the open position with the animal sedated, the animal handler will place the syringe into the bloodstream of the laboratory animal and will run a line from the syringe 80 through the access slot 34 into the pocket 30 of the jacket 10. A catheter 82 will then be secured to the end of the medical communication line and the catheter will thereby be retained within the pocket 30.

The animal handler will then close the pocket 30 and will activate the pocket retaining loop 62 and may also secure the locking tie means 64 to affix the pocket zipper 36 in the closed position. The animal handler can then close the main fastening zipper 26 to secure the jacket upon the laboratory animal 8. Thereafter the size of the neck opening 18 can be restricted by tightening of the neck band 72 to the tightest position which allows engagement of the neck button 76 with respect to the neck button holes 74.

In a similar fashion the animal handler can tighten the abdominal band member 52 by securing of the button 54 in the tightest possible position of the button hole 56 as determined by the size of the abdominal area of the laboratory animal 8.

The main clip means 42 can be positioned to extend through the main tab 44 of the main fastening zipper 26 as well as to extend around the abdominal band member 52. In this manner the main fastening zipper 26 will be retained in place.

Once the jacket 10 is in this manner placed upon the laboratory animal 8 convenient access to the interior of the pocket 30 by the investigators is made possible thereby greatly facilitating reliability of testing and research data gathered thereby. There is no requirement that the jacket member 10 be removed or replaced each time there is testing or the taking of data occurring. Also, the dangers of self-inflicted injuries by access of the laboratory animal to either the pocket zipper or the main zipper is eliminated. These advantages are achieved by the strategic positioning of the access slot 34 within a lockable pocket 30 with a separate main locking means for the jacket 10. This combination provides the unique advantages of the present invention.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. An improved laboratory animal restraining jacket with a sealable medical device holding pocket which comprises:

A. a jacket member including a front section and a rear section, said front section and said rear section defining a neck opening means, an abdominal opening means and arm opening means therebetween, said rear section of said jacket member including a main opening slit means extending from said neck opening means to said abdominal opening means to facilitate placement and removal of said jacket member upon a laboratory animal;

B. a main fastening means positioned adjacent said main opening slit means of said rear section of said jacket member, said main fastening means adapted to selectively close and open said main opening slit means as desired in order to facilitate placement and removal of said jacket member upon a laboratory animal;

C. a flap means positioned on the exterior of said jacket member and defining a pocket means therebetween, said flap means and said jacket member defining a pocket opening means in communication with respect to said pocket means to facilitate access thereinto, said jacket member defining an access slot extending therethrough adjacent said flap means and within said pocket means to allow placement of a medical device from within said pocket means to extend through said access slot for direct access to a laboratory animal positioned within said jacket member, said access slot providing access from said pocket means to within said jacket member;

D. a pocket fastening means extending along said pocket opening means, said pocket fastening means being adapted to selectively close and open said pocket opening means as desired in order to facilitate access to said pocket means; and E. a main covering means positioned adjacent said main opening slit means and adjacent said main fastening means, said main covering means adapted to extend over said main fastening means and selectively engage said jacket member thereacross to prevent access to said main fastening means from the exterior of said jacket member.

2. An improved laboratory animal restraining jacket with a sealable medical device holding pocket as defined in claim 1 further comprising a main hook and loop engagement means positioned adjacent said main covering means and said jacket member to facilitate engagement therebetween for covering of said main fastening means 3. An improved laboratory animal restraining jacket with a sealable medical device holding pocket as defined in claim 1 wherein said arm opening means comprises two arm opening holes defined between said front section and said rear section of said jacket member.

4. An improved laboratory animal restraining jacket with a sealable medical device holding pocket as defined in claim 1 wherein said main fastening means comprises a main zipper means.

5. An improved laboratory animal restraining jacket with a sealable medical device holding pocket as defined in claim 4 wherein said main zipper means is in the closed position responsive to being in the lowermost position adjacent said abdominal opening means.

6. An improved laboratory animal restraining jacket with a sealable medical device holding pocket as defined in claim 5 further comprising a main clip means attached with respect to said jacket member adjacent said abdominal opening means and wherein said main zipper means includes a main tab means attached thereto, said main clip means being engageable with respect to said main tab means to retain said main zipper means in the closed position adjacent said abdominal opening.

7. An improved laboratory animal restraining jacket with a sealable medical device holding pocket as defined in claim 1 further including a peripheral abdominal channel means and a first abdominal channel aperture and a second abdominal channel aperture defined by said jacket member adjacent said abdominal opening means therein, and further including an abdominal band member positioned extending through said first abdominal channel aperture and through said peripheral abdominal channel means and through said second abdominal aperture, said abdominal band member adapted to retain said abdominal opening means immediately adjacent to the abdomen of a laboratory animal.

8. An improved laboratory animal restraining jacket with a sealable medical device holding pocket as defined in claim 7 wherein said abdominal band member defines a plurality of abdominal button holes and includes an abdominal button means securable with respect to said abdominal button holes to facilitate tightening of said abdominal band member.

9. An improved laboratory animal restraining jacket with a sealable medical device holding pocket as defined in claim 1 wherein said pocket fastening means comprises a pocket zipper means.

10. An improved laboratory animal restraining jacket with a sealable medical device holding pocket as defined in claim 9 wherein said pocket zipper means is in the closed position responsive to being in the uppermost position closest to said neck opening means.

11. An improved laboratory animal restraining jacket with a sealable medical device holding pocket as defined in claim 10 further comprising a pocket retaining means attached with respect to said jacket member adjacent said pocket means and wherein said pocket zipper means includes a pocket tab means attached thereto, said pocket retaining means being engageable with respect to said pocket tab means to retain said pocket zipper means in the closed position.

12. An improved laboratory animal restraining jacket with a sealable medical device holding pocket as defined in claim 11 wherein said pocket retaining means comprises a loop means being engageable with respect to said pocket tab means of said pocket zipper means.

13. An improved laboratory animal restraining jacket with a sealable medical device holding pocket as defined in claim 12 further comprising a locking tie means engageable with respect to said pocket tab means and with respect to said jacket member to facilitate holding of said pocket zipper means in the closed position.

14. An improved laboratory animal restraining jacket with a sealable medical device holding pocket as defined in claim 1 further including a peripheral neck channel means and a first neck channel aperture and a second neck channel aperture defined by said jacket member adjacent said neck opening means therein, and further including a neck band member positioned extending through said first neck channel aperture and through said peripheral neck channel means and through said second neck aperture, said neck band member adapted retain said neck opening means immediately adjacent to the neck of a laboratory animal.

15. An improved laboratory animal restraining jacket with a sealable medical device holding pocket as defined in claim 14 wherein said neck band member defines a plurality of neck button holes and includes a neck button means securable with respect to said neck button holes to facilitate tightening of said neck band member.

16. An improved laboratory animal restraining jacket with a sealable medical device holding pocket as defined in claim 1 wherein said jacket member is made of an open weave material.

17. An improved laboratory animal restraining jacket with a sealable medical device holding pocket as defined in claim 1 wherein said jacket member is made of an open weave polyester material.

18. An improved laboratory animal restraining jacket with a sealable medical device holding pocket as defined in claim 1 further including an additional layer of material extending over a portion of said front section of said jacket member to facilitate strengthening thereof.

19. An improved laboratory animal restraining jacket with a sealable medical device holding pocket as defined in claim 1 wherein said access slot is defined in said jacket member within said pocket means adjacent said flap means.

20. An improved laboratory animal restraining jacket with a sealable medical device holding pocket which comprises:

A. a jacket member of open weave polyester material which includes a front section and a rear section, said front section and said rear section defining a neck opening means, an abdominal opening means and two arm opening means therebetween, said rear section of said jacket member including a main opening slit means extending from said neck facilitate placement and removal of said jacket member upon a laboratory animal, said jacket member further defining a peripheral abdominal channel means and a first abdominal channel aperture and a second abdominal channel aperture located adjacent said abdominal opening means therein, said jacket member further defining a peripheral neck channel means and a first neck channel aperture and a second neck channel aperture adjacent said neck opening means therein;

(1) an abdominal band member positioned extending through said first abdominal channel aperture and through said peripheral abdominal channel means and through said second abdominal aperture, said abdominal band member adapted to retain said abdominal opening means immediately adjacent to the abdomen of a laboratory animal, said abdominal band member defining a plurality of abdominal button holes and including an abdominal button means securable with respect to said abdominal button holes to facilitate tightening of said abdominal band member;

(2) a neck band member positioned extending through said first neck channel aperture and through said peripheral neck channel means and through said second neck aperture, said neck band member adapted retain said neck opening means immediately adjacent to the neck of a laboratory animal, said neck band member defining a plurality to neck button holes and including a neck button means securable with respect to said neck button holes to facilitate tightening of said neck band member;

B. a main fastening means comprising a main zipper means positioned adjacent said main opening slit means of said rear section of said jacket member, said main fastening means adapted to selectively close and open said main opening slit means as desired in order to facilitate placement and removal of said jacket member upon a laboratory animal, said main zipper means being in a closed position respective to being in the lowermost position adjacent said abdominal opening means, said main zipper means including a main tab means attached thereto;

C. a flap means positioned on the exterior of said jacket member and defining a pocket means therebetween, said flap means and said jacket member defining a pocket opening means in communication with respect to said pocket means to facilitate access thereto said jacket member defining an access slot extending therethrough adjacent said flap means and within said pocket means to allow placement of a medical device from within said pocket means to extend through said access slot for direct access to a laboratory animal positioned within said jacket member, said access slot providing access from said pocket means to within said jacket member;

D. a pocket fastening means comprising a pocket zipper means extending along said pocket opening means, said pocket fastening means being adapted to selectively close and open said pocket opening means as desired in order to facilitate access to said pocket means, said pocket zipper means being in the closed position responsive to being in the uppermost position closest to said neck opening means, said pocket zipper means including a pocket tab means attached thereto;

E. a main covering means positioned adjacent said main opening slit means and adjacent said main fastening means, said main covering means adapted to extend over said main fastening means and selectively engage said jacket member thereacross to prevent access to said main fastening means from the exterior of said jacket member;

F. a main hook and loop engagement means positioned adjacent said main covering means and said jacket member to facilitate engagement therebetween to facilitate selective covering of said main fastening means;

G. a main clip means attachable to said abdominal band means and to said main tab means to retain said main zipper means in the closed position adjacent said abdominal opening means H. a pocket retaining loop mean attached with respect to said jacket member adjacent said pocket means, said pocket retaining loop means being engageable with respect to said pocket tab mean to retain said pocket zipper means int he closed position;

I. a locking tie means engageable with respect to said pocket tab means and with respect to said jacket member to facilitate selective holding of said pocket zipper means in the closed position; and J. a strengthening layer of material extending over a portion of said front section of said jacket member to facilitate strengthening thereof.

* * * * *

UNITED STATES PATENT AND TRADEMARK OFFICE
CERTIFICATE OF CORRECTION

PATENT NO. : 5,293,840
DATED : March 15, 1994
INVENTOR(S) : Susan Wedlick

It is certified that error appears in the above-identified patent and that said Letters Patent is hereby corrected as shown below:

Col. 11,
In Claim 20(A), line 7, after "neck" insert -- opening means to said abdominal opening means to --.
Col. 11,
In Claim 20(B), line 50, change "respective" to -- responsive --.
Col. 12,
In Claim 20(H), line 45, change "int he" to -- in the --.
Col. 12,
In Claim 20(H), line 44, change "mean" to -- means --.

Signed and Sealed this

Fourth Day of April, 1995

Attest:

BRUCE LEHMAN

*Attesting Officer*     *Commissioner of Patents and Trademarks*